United States Patent
Heraty et al.

(10) Patent No.: US 10,966,847 B2
(45) Date of Patent: Apr. 6, 2021

(54) MEDICAL DEVICE SUITABLE FOR LOCATION IN A BODY LUMEN

(71) Applicants: Kevin Heraty, County Galway (IE); Liam Mullins, Galway (IE); Paul Gilson, County Galway (IE); Martin G. Burke, West Sussex (GB)

(72) Inventors: Kevin Heraty, County Galway (IE); Liam Mullins, Galway (IE); Paul Gilson, County Galway (IE); Martin G. Burke, West Sussex (GB)

(73) Assignee: Veryan Medical Limited, Oxford (GB)

( * ) Notice: Subject to any disclaimer, the term of this patent is extended or adjusted under 35 U.S.C. 154(b) by 431 days.

(21) Appl. No.: 15/211,997

(22) Filed: Jul. 15, 2016

(65) Prior Publication Data

US 2016/0324667 A1 Nov. 10, 2016
US 2019/0151123 A9 May 23, 2019

Related U.S. Application Data

(63) Continuation-in-part of application No. 12/249,424, filed on Oct. 10, 2008, now Pat. No. 9,539,120, and
(Continued)

(30) Foreign Application Priority Data

Oct. 10, 2008 (EP) ..................................... 08253319

(51) Int. Cl.
*A61F 2/88* (2006.01)
*A61F 2/91* (2013.01)
*A61F 2/844* (2013.01)

(52) U.S. Cl.
CPC ............... *A61F 2/88* (2013.01); *A61F 2/844* (2013.01); *A61F 2/91* (2013.01);
(Continued)

(58) Field of Classification Search
CPC .............. A61F 2210/00023; A61F 2/82; A61F 2230/0091; A61F 2/88; A61F 2250/0039;
(Continued)

(56) References Cited

U.S. PATENT DOCUMENTS 5,449,373 A 9/1995 Pinchasik et al.
5,938,697 A 8/1999 Killion et al.
(Continued)

FOREIGN PATENT DOCUMENTS

DE 102005050386 A1 * 4/2007 ............... A61F 2/95
EP 0 800 801 A1 10/1997
(Continued)

OTHER PUBLICATIONS

Abstract of DE102005050386 (Year: 2007).*
(Continued)

*Primary Examiner* — Brian E Pellegrino
(74) *Attorney, Agent, or Firm* — Fay Sharpe LLP (57) ABSTRACT

A medical device suitable for location in a body lumen is movable between a first loaded configuration and a second loaded configuration. The device has an unloaded configuration which is intermediate the first loaded configuration and the second loaded configuration. The device can be a stent for deployment in a blood vessel.

15 Claims, 9 Drawing Sheets

Related U.S. Application Data a continuation of application No. 13/123,117, filed as application No. PCT/GB2009/002434 on Oct. 12, 2009, now abandoned.

(52) U.S. Cl.
CPC .............. *A61F 2230/0054* (2013.01); *A61F 2250/0096* (2013.01); *A61F 2310/00023* (2013.01); *Y10S 623/903* (2013.01)

(58) Field of Classification Search
CPC ...... A61F 2210/0014; A61F 2210/0023; A61F 2202/047; A61F 2/95; A61F 2/844; A61F 2250/0096; Y10S 623/903
See application file for complete search history.

(56) References Cited

U.S. PATENT DOCUMENTS

| | | | |
|---|---|---|---|
| 6,001,123 A * | 12/1999 | Lau | A61F 2/88 606/194 |
| 6,270,524 B1 | 8/2001 | Kim | |
| 6,896,697 B1 | 5/2005 | Yip et al. | |
| 7,018,401 B1 | 3/2006 | Hyodoh et al. | |
| 7,625,400 B2 | 12/2009 | Bowe et al. | |
| 7,731,747 B2 | 6/2010 | Kaplan et al. | |
| 8,226,704 B2 | 7/2012 | Caro et al. | |
| 8,236,043 B2 | 8/2012 | Caro et al. | |
| 8,425,585 B2 | 4/2013 | Melsheimer et al. | |
| 8,882,826 B2 | 11/2014 | Ta et al. | |
| 2001/0025130 A1 | 9/2001 | Tomonto | |
| 2002/0179166 A1 | 12/2002 | Houston et al. | |
| 2002/0183853 A1 | 12/2002 | Mitchell et al. | |
| 2003/0088305 A1 | 5/2003 | Van Schie et al. | |
| 2003/0187497 A1 | 10/2003 | Boylan et al. | |
| 2004/0087997 A1 * | 5/2004 | Brenneman | A61F 2/88 606/200 |
| 2004/0117004 A1 * | 6/2004 | Osborne | A61F 2/07 623/1.36 |
| 2005/0096733 A1 | 5/2005 | Kovneristy et al. | |
| 2006/0030926 A1 | 2/2006 | Berra | |
| 2006/0064120 A1 | 3/2006 | Levine et al. | |
| 2006/0217795 A1 | 9/2006 | Besselink et al. | |
| 2006/0265051 A1 | 11/2006 | Caro et al. | |
| 2007/0055299 A1 | 3/2007 | Ishimaru et al. | |
| 2007/0191927 A1 | 8/2007 | Bowe et al. | |
| 2008/0086854 A1 | 4/2008 | Boyd et al. | |
| 2008/0262599 A1 | 10/2008 | Caro et al. | |
| 2008/0306440 A1 | 12/2008 | Hirszowicz et al. | |
| 2009/0149945 A1 | 6/2009 | Pike | |
| 2009/0234431 A1 | 9/2009 | Weinberger et al. | |
| 2010/0094403 A1 | 4/2010 | Heraty et al. | |
| 2010/0286759 A1 | 11/2010 | Taylor et al. | |
| 2012/0283819 A1 | 11/2012 | Taylor et al. | |
| 2012/0330402 A1 | 12/2012 | Vad et al. | |

FOREIGN PATENT DOCUMENTS

| | | |
|---|---|---|
| EP | 0 951 877 | 10/1999 |
| EP | 1 279 382 A1 | 1/2003 |
| EP | 2 174 623 A1 | 4/2010 |
| EP | 2 174 624 A1 | 4/2010 |
| GB | 2 418 362 A | 3/2006 |
| GB | 2 425 485 | 11/2006 |
| JP | H 11-332998 | 12/1999 |
| JP | 2002-535075 A | 10/2002 |
| JP | 2005-013302 | 1/2005 |
| JP | 2007-144108 A | 6/2007 |
| JP | 2008-513171 | 5/2008 |
| WO | WO 98/20810 | 5/1998 |
| WO | WO 00/44308 | 8/2000 |
| WO | WO 03/059199 A1 | 7/2003 |
| WO | WO 2006/032902 | 3/2006 |
| WO | WO 2007/053791 A1 | 5/2007 |
| WO | WO 2007/062661 A1 | 6/2007 |
| WO | WO 2008/117256 A2 | 10/2008 |
| WO | WO 2008/125842 A1 | 10/2008 |
| WO | WO 2010/128311 A1 | 11/2010 |

OTHER PUBLICATIONS

Description translation of DE102005050386 (Year: 2007).*
European Search Report corresponding to EP 08 25 3319, dated Jan. 15, 2009 (English Text).
Cheng, Christopher P. (Editor), "Handbook of Vascular Motion", Academic Press, Copyright 2019 Elsevier Inc., 22 miscellaneous pages of 413.

* cited by examiner

MEDICAL DEVICE SUITABLE FOR LOCATION IN A BODY LUMEN

This application is a continuation of U.S. patent application Ser. No. 13/123,117 which was filed on Sep. 1, 2011 and is still pending. That application in turn was the national phase of International Application Serial No. PCT/GB2009/002434 which was filed on Oct. 12, 2009 and which claims priority to U.S. patent application Ser. No. 12/249,424 which was filed on Oct. 10, 2008 and European Patent Application Serial No. 08253319.1 which was filed on Oct. 10, 2008.

INTRODUCTION

This invention relates to a medical device suitable for location in a body lumen.

STATEMENTS OF INVENTION

According to the invention there is provided a medical device suitable for location in a body lumen, the device being movable between a first loaded configuration and a second loaded configuration, the device having an unloaded configuration intermediate the first loaded configuration and the second loaded configuration. The degree of deformation which the device undergoes moving from the unloaded configuration to either the first loaded configuration or the second loaded configuration is less than the device would undergo moving directly from the first loaded configuration to the second loaded configuration.

In one embodiment of the invention the device is suitable for location in a body lumen which is movable between an unloaded state and a loaded state. Preferably the device is configured to be in the first loaded configuration when a body lumen is in an unloaded state. Ideally the device is configured to be in the second loaded configuration when a body lumen is in a loaded state.

The device may be deformable between the first loaded configuration and the second loaded configuration. In one case the device is bendable between the first loaded configuration and the second loaded configuration. The device may be twistable between the first loaded configuration and the second loaded configuration. The device may be compressible between the first loaded configuration and the second loaded configuration.

The device may be configured to minimise the strains which it experiences during movement between configurations. This can be achieved because the unloaded configuration of the device is intermediate the first loaded configuration and the second loaded configuration. Reduced strains give reduced risk of fracture and an increased fatigue resistance. The maximum strain may reduce as the device moves from the first loaded configuration to the unloaded intermediate configuration, and then increase as the device moves from the unloaded intermediate configuration to the second loaded configuration.

It is known from EP 1279382 to provide a curved stent in which the shape of the stent is matched to the shape of the vessel, the purpose being to minimise the strains in the stent when it is initially deployed. If the shape of the vessel then changes to an extreme position, the stent will be loaded and the stent will experience strains based on a deformation of the stent from its initial natural configuration to the extreme position. In contrast, at least in the preferred embodiments of the invention, the shape of the device, e.g. stent, is matched to a configuration intermediate two opposing extremes. The device will experience strains based on a deformation of the device from its natural configuration which is intermediate the two opposing extremes to respective configurations at those extremes. Thus the maximum strains experienced by the device can be reduced as compared to the technique of EP 1279382.

The maximum strain experienced anywhere in the device of the invention can be determined by finite element analysis. For example in the case of a stent having a given stent wall pattern, if the loading is known then the strains can be calculated.

If the medical device is delivered when the body lumen is in the unloaded state, it may be delivered in its first loaded configuration. For example if the body lumen is straight when in the unloaded state, then the device may be delivered in a curved configuration, so as then to be caused by the body lumen to adopt the first loaded configuration. The medical device may be contained in a delivery device, such as a catheter, pre-set in the curved configuration.

In the unloaded configuration at least part of the longitudinal axis of the device may be curved in a two-dimensional plane. The device, for example a stent, may be curved through an angle. The angle through which the device is curved (the "curve angle") is the angle between the longitudinal axis of the device at one end thereof and a line from a point on the longitudinal axis at that end to a point on the longitudinal axis at the other end of the device.

In certain preferred embodiments, the device is configured so that when the device is deformed through a curve angle of 45 degrees between the first loaded configuration and the second loaded configuration, the maximum strain in the device, at any stage at or between the first and second loaded configurations, is 0.4% or 0.3% or 0.2%. For example a stent may be substantially straight when in the first loaded configuration and curved through a curve angle of 45 degrees when in the second loaded configuration, with a maximum strain of less than or equal to 0.4% or 0.3%. In contrast a stent which bends from an initial unloaded configuration which is substantially straight, through a curve angle of 45 degrees, may experience a maximum strain of 0.45% or more.

A common choice of material for making stents is Nitinol, and the strain limit for repeated loading of Nitinol without it suffering fatigue failure is 0.4%. Hence the preferred embodiments in which the maximum strain is kept below this limit can be made of Nitinol.

In the unloaded configuration at least part of the longitudinal axis of the device may be curved in three-dimensional space. Preferably in the unloaded configuration at least part of the device is substantially helically shaped, for example the longitudinal axis of that part may be substantially helical.

In certain preferred embodiments, the device is configured so that when the device is axially compressed by 6% from the first loaded configuration to the second loaded configuration, the maximum strain in the device, at any stage at or between the first and second loaded configurations, is less than or equal to 0.7%. This may for example be achieved by devices with plural curves in one plane, e.g. sinusoidal or substantially zigzag in shape, or by helically shaped devices. A maximum strain in the device of less than or equal to 0.6% or 0.5% or 0.4% or 0.3% may be achieved. In one example the maximum strain at 6% axial compression is 0.2%. In contrast a stent which undergoes axial compression from an initial unloaded configuration which is substantially straight, may experience at 4.5% axial compression a maximum strain of 0.8%, and at 5% axial compression a maximum strain of 1.6% which may cause fatigue fracture when the load is applied repeatedly.

The unloaded configuration may be approximately midway between the first loaded configuration and the second loaded configuration.

The device may comprise means to align the device relative to a body lumen.

Preferably the alignment means comprises means to visualise the device. Ideally the alignment means comprises one or more markers on the device. The alignment means is preferably rotational alignment means. For example, in the case of a curved device (whether curved in a two-dimension plane or in three-dimensional space), the provision of rotational alignment means enables the curvature of the device to be generally aligned with the curvature of a body lumen.

The device may be suitable for location in a blood vessel. Preferably the device comprises a stent suitable for deployment in a blood vessel. In one case the invention provides a stent with geometry optimised for vessel deformation. The stent may be a stent graft.

There are various blood vessels which are movable between an unloaded state and a loaded state in which stents in accordance with preferred embodiments of the invention may be used. These include vessels at or near joints in the body, such as the elbow, hip or knee. In particular the stent may be suitable for deployment in the popliteal artery behind the knee, or the superficial femoral artery above the knee. It may be suitable for the iliac artery at the hip joint. Large degrees of bending take place at the elbow or knee.

Other blood vessels which are movable between an unloaded state and a loaded state, in which stents in accordance with preferred embodiments of the invention may be used, include stents used for coronary arteries and the carotid artery. Coronary arteries extend on the surface of the heart and as it beats the surface curvature oscillates between the systole and the diastole modes. Stents of the invention may therefore provide benefits in reducing the strains experienced during the repeated curvature changes. The carotid arteries in the neck may deform when the neck is bent, so stents of the invention may be advantageously used.

For certain stents, in the unloaded configuration at least part of the longitudinal axis of the stent may be curved in a two-dimensional plane. In the case of a joint where bending takes place, it may be desirable to deploy the stent so that the plane in which the stent is curved corresponds to the plane in which the bending at the joint takes place, for example the plane in which a leg bends during sitting down. This may be achieved using means to align the device relative to a body lumen.

Axial compression of the superficial femoral artery takes place when the leg is moved from a straight state to a bent state, causing large strains in conventional stents which tend to be in an unloaded configuration when the leg is straight. These strains can be significantly reduced by using a stent of the present invention which is arranged to be loaded when the leg is straight, unloaded when the leg is partly bent, and loaded again when the leg is more fully bent.

The invention also provides a method of stenting a body lumen, the method comprising deploying a stent in a body lumen which is movable between an unloaded state and a loaded state, the stent being movable between a first loaded configuration and a second loaded configuration, and the method comprising deploying the stent in the body lumen so that when the body lumen is in the unloaded state the stent is in the first loaded configuration, and so that when the body lumen is in the loaded state the stent is in the second loaded configuration.

Preferably, when the body lumen is in an intermediate state, between the unloaded state and the loaded state, the stent is in an unloaded configuration.

If the stent is delivered when the body lumen is in the unloaded state, it may be delivered in its first loaded configuration. For example if the body lumen is straight when in the unloaded state, then the stent may be delivered in a curved configuration, so as then to be caused by the body lumen to adopt the first loaded configuration. The stent may be contained in a delivery device, such as a catheter, pre-set in the curved configuration.

In a preferred method, in the unloaded configuration at least part of the longitudinal axis of the stent is curved. The curvature may be in a two-dimensional plane or it may be in three-dimensional space.

In the case of curvature in a two-dimensional plane, the method may comprise deploying the stent at a joint of the body where bending movement takes place, the deployment being made so that the plane in which the stent is curved corresponds to the plane in which the bending movement at the joint takes place. Diameters as referred to in this specification are the internal diameters. Preferred embodiments of stent have a diameter in the range of 2 mm to 10 mm. Diameters in the range of 5 mm to 8 mm are preferred for use in the knee, above the knee or in the elbow. Diameters in the range of 5 mm to 10 mm are preferred for use in the iliac artery. Diameters in the range of 2 mm to 4 mm are preferred for use in the coronary arteries.

Lengths as referred to in this specification are the lengths from end to end along the longitudinal axis, following any curvature of that axis. Certain preferred embodiments of stent have a length of at least 40 or 50 or 60 or 70 or 80 or 90 or 100 or 110 or 120 or 130 or 140 or 150 or 160 or 170 or 180 or 190 or 200 mm. These embodiments are suited for use as peripheral stents, for example in the knee, above the knee or in the elbow. Certain preferred embodiments of stent have a length of at least 15 or 20 or 25 or 30 or 35 mm. Shorter stents are suited to use in the coronary arteries for example.

Preferred embodiments of stent have a length to diameter ratio of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40. The risk of buckling is increased when stents with smaller length to diameter ratios are subjected to bending loads.

Certain preferred devices, such as stents, have a substantially helical longitudinal axis. This helical axis has an amplitude, which is the extent of displacement from a mean position to a lateral extreme. So the amplitude is one half of the full lateral width of the helical axis. In this specification, the term "relative amplitude" of the helical axis means the amplitude divided by the diameter. For preferred helical stents, the relative amplitudes in the various configurations of use can range between 0 and 2, or 0 and 1.5. For example, the relative amplitude in the first loaded configuration may be in the range of 0 to 0.5, in the unloaded intermediate configuration (i.e. as manufactured) in the range of 0.3 to 0.7, 0.8 or 0.9, and in the second loaded configuration in the range of 0.5 and above, for example up to 1.5 or 2.

Embodiments of the helical stents may have a pitch in the unloaded intermediate configuration (i.e. as manufactured) in the range of 20 to 70 mm, 30 to 60 mm, 40 to 50 mm, 20 to 30 mm, 30 to 40 mm, 40 to 50 mm, 50 to 60 mm, or 60 to 70 mm. One example has a pitch of 45 mm.

Embodiments of the helical stents may have a pitch in the unloaded intermediate configuration (i.e. as manufactured) in the range of 5 to 20 mm, 10 to 15 mm, 5 to 10 mm, 10 to 15 mm, or 15 to 20 mm. Shorter pitches may be used with smaller stents, i.e. stents which are shorter or have smaller diameters or both. Shorter pitches are suited to use in the coronary arteries for example. A pitch of 6 mm may for example be used in a coronary stent.

When a helical stent is subjected to axial compression, the effect will be for the amplitude (and hence the relative amplitude) to be increased and the pitch to be decreased. A helical stent can undergo these changes without experiencing excessive strains.

BRIEF DESCRIPTION OF THE DRAWINGS

The invention will be more clearly understood from the following description of some embodiments thereof, given by way of example only, with reference to the accompanying drawings, in which.

DETAILED DESCRIPTION

Figure 1:
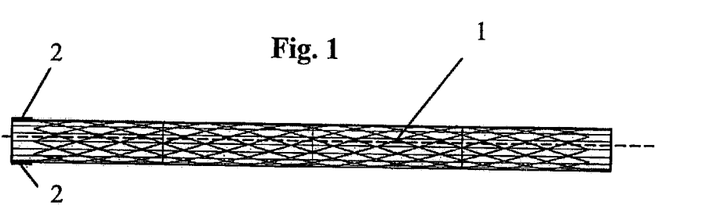
FIG. 1 is a side view of a medical device according to the invention in a first loaded configuration located in a body lumen.
Figure 2:
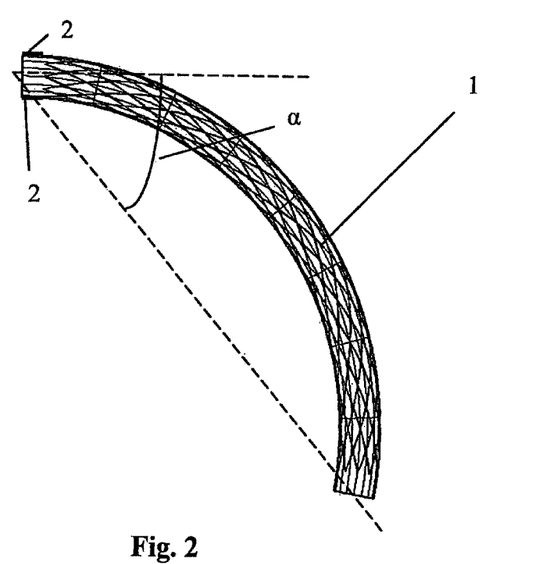
FIG. 2 is a side view of the device of FIG. 1 in a second loaded configuration located in the body lumen.
Figure 3:
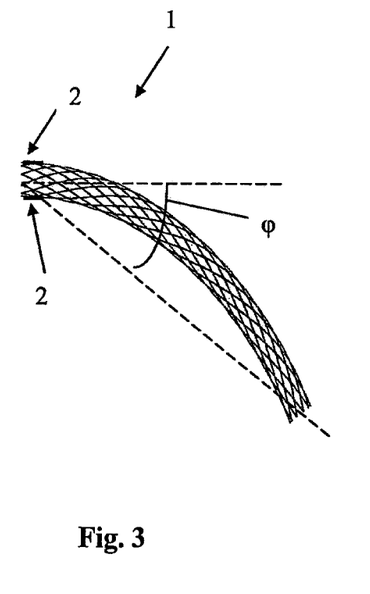
FIG. 3 is a side view of the device of FIG. 1 in an unloaded configuration.

Referring to the drawings, and initially to FIGS. 1 to 3 thereof, there is illustrated a medical device 1 according to the invention suitable for location in a body lumen. The medical device 1 is movable between a first loaded configuration (FIG. 1) and a second loaded configuration (FIG. 2).

In this case the medical device 1 comprises a stent suitable for deployment in a blood vessel which is movable between an unloaded straight cylindrical state (FIG. 1) and a loaded curved state (FIG. 2). The stent 1 supports at least part of an internal wall of the blood vessel. The stent 1 is in the first loaded configuration when the blood vessel is in the unloaded state (FIG. 1), and the stent 1 is in the second loaded configuration when the blood vessel is in the loaded state (FIG. 2).

The stent 1 is bendable through a single bend between the first loaded configuration (FIG. 1) and the second loaded configuration (FIG. 2).

The stent 1 has an unloaded configuration (FIG. 3) which is intermediate the first loaded configuration and the second loaded configuration. In the unloaded configuration the stent 1 is in a rest state. In this case the unloaded configuration is approximately midway between the first loaded configuration and the second loaded configuration. In the unloaded configuration the longitudinal axis of the stent 1 is curved through a single bend in a two-dimensional plane. In this case no shape change occurs upon delivery of the stent 1 to the blood vessel. The stent 1 has the same unloaded configuration outside of the blood vessel prior to delivery and after deployment in the blood vessel.

The stent 1 may be balloon expandable or self-expanding.

The stent 1 is suitable for use in the blood vessel which is subject to tortuous loading, such as bending. The stent 1 has the pre-set curved geometry in the unloaded configuration, as shown in FIG. 3. The choice of pre-set curve is determined by the extremes of deformation which occur in the blood vessel in which the stent 1 will be implanted. The unloaded configuration of the stent 1 represents a configuration between two opposing extremes of deformation of the blood vessel, such as those shown in FIGS. 1 and 2.

Because of physiological movements within the body, the blood vessel may be forced to adopt tortuous configurations. Large degrees of bending may occur, for example with bends in excess of 90°, for example up to 140°. A bend between limb parts at a joint means the angle between the limb parts measured at the joint, for example the angle between the lower leg and the upper leg at the knee. Such a bend at the joint corresponds to a smaller "curve angle" of the stent as defined above, for example a bend at the joint of 90° may result in a curve angle of the stent of 45°, whilst a bend at the joint of 140° may result in a curve angle of the stent of 70°.

The location for the stent 1 may be in the blood vessel in the leg behind the knee which is subject to frequent bending as the patient bends the leg. Because the unloaded configuration of the stent 1 is non-straight, the degrees of deformation which the stent 1 undergoes are minimised leading to minimised strains, increased fatigue life, and reduced risk of fracture. The configuration of FIGS. 1 to 3 results in the stent 1 bending by a maximum of $\varphi$ degrees, that is from $\varphi$ degrees to 0 degrees (FIG. 3 to FIG. 1), or from $\varphi$ degrees to $\alpha$ degrees (FIG. 3 to FIG. 2). In this case $\alpha=2\varphi$. This contrasts with the conventional approach of bending a stent by $\alpha$ degrees each time, that is from 0 degrees to $\alpha$ degrees (FIG. 1 to FIG. 2).

Each of the angles $\alpha$ degrees and $\varphi$ degrees through which the device is curved is a "curve angle", i.e. the angle between the longitudinal axis of the device at one end thereof and a line from a point on the longitudinal axis at that end to a point on the longitudinal axis at the other end of the device.

FIGS. 1 to 3 illustrate a single bend in one plane. FIG. 1 illustrates the stent 1 deployed in the unloaded vessel, FIG. 2 illustrates the stent 1 deployed in the loaded vessel, and FIG. 3 illustrates the stent 1 in the unloaded configuration.

Since some of the deformation of the blood vessel is already incorporated in the stent 1 in the unloaded configuration (FIG. 3), the strains induced through further deformation of the stent 1 to achieve the fully loaded configuration (FIG. 2) are less than those which would be induced if the stent 1 had to go from the straight (FIG. 1) to the fully loaded configuration of the blood vessel (FIG. 2).

For example, as shown in FIGS. 1 to 3, in a blood vessel which bends between 0 degrees and α degrees in one plane, the curved stent 1 in the unloaded configuration already accommodates the angle of φ degrees. Therefore in order to bend from 0 degrees to α degrees, the stent 1 bends from (−φ) degrees to (α−φ) degrees. Improved mechanical performance is achieved since the induced strains at angles of (−φ) degrees and (α−φ) degrees are less than those induced by bending a straight stent from 0 degrees to α degrees. The stent 1 comprises visualisation means to align the stent 1 relative to the blood vessel. In this case the alignment means comprises one or more markers 2 on the stent 1. A pair of markers 2 are provided in this embodiment, both at one end of the stent 1 and positioned diametrically opposite each other. The stent 1 may be oriented at the implantation site, for example using the radiopaque markers or other visualisation means. The rotational position of the stent may be adjusted during implantation whilst using the markers to visualise the rotational position. The stent 1 may be aligned with the axis of bending of the knee of a patient during deployment.

In use, the stent 1 is delivered into the blood vessel and deployed at a desired treatment site in the blood vessel. The stent 1 may be oriented at the desired treatment site.

As the blood vessel moves from the unloaded straight cylindrical state (FIG. 1) to the loaded curved state (FIG. 2), the stent 1 bends from the first loaded configuration to the second loaded configuration.

The operation of the stent of FIGS. 1 to 3 when inserted in a leg will be described with reference to FIG. 10.

Figure 10:
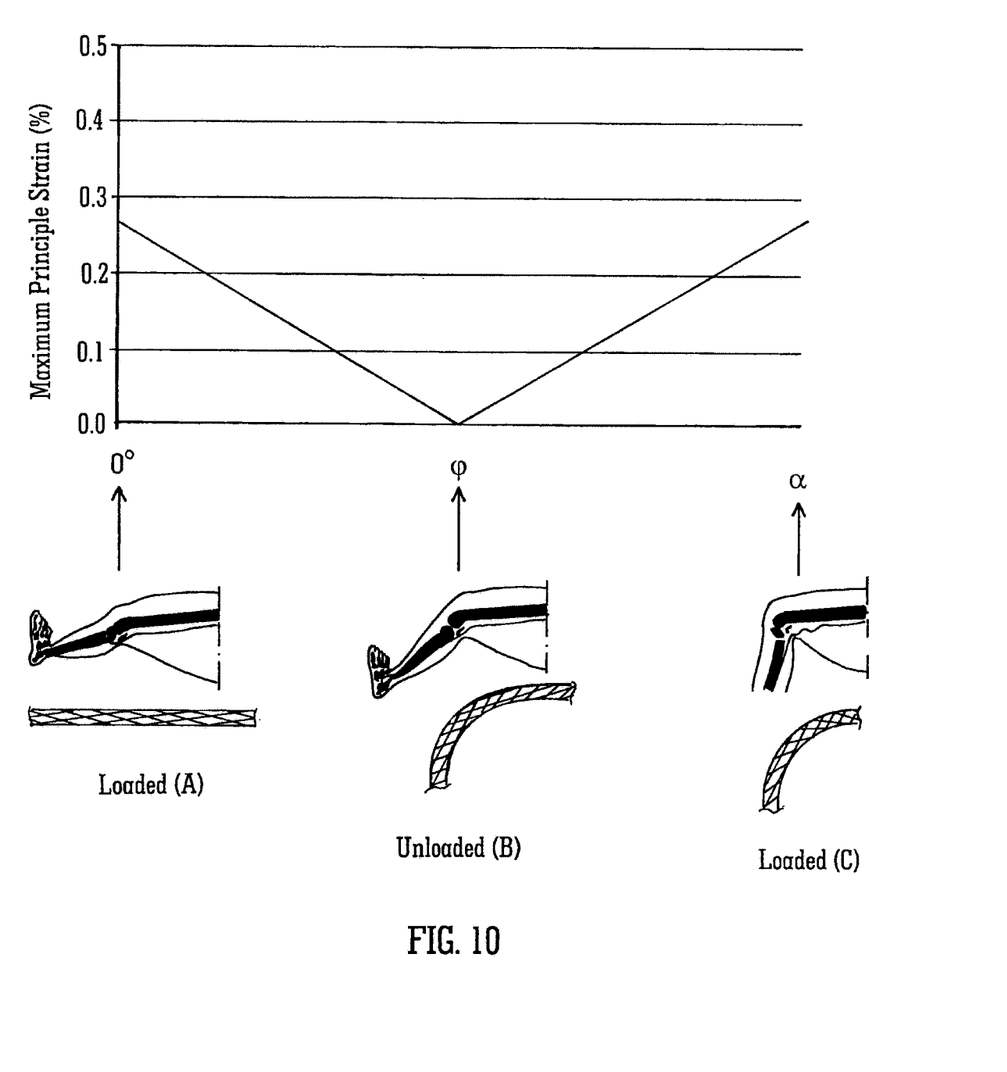
FIG. 10 shows three configurations of the stent of FIGS. 1 to 3 and a graph showing the maximum principal strains in the stent at different angles of deformation.

FIG. 10 shows three configurations of the stent, at three leg positions A, B and C.

The leg is substantially straight in position A and at this time the stent is in a first loaded configuration corresponding to FIG. 1. The leg is in a partially bent condition in position B and the stent is then in the unloaded configuration corresponding to FIG. 3, bent at an angle of φ degrees. The leg is in a more bent condition at position C, corresponding to FIG. 2, when the stent is bent at an angle of α degrees.

Finite element analysis was used to evaluate the strains which occur during bending of the leg from the straight condition shown as position A to the sitting condition shown as position C. The results are shown in the graph of FIG. 10. When the leg is straight, the stent has been bent through an angle of −φ degrees and the maximum principle strain in the stent is approximately 0.27%. When the leg is partially bent, and the stent has a bend angle of φ degrees it is in the unloaded configuration. Therefore, at this angle, because the stent is unloaded, the strains in the stent are zero. As the leg is bent further, to an angle of α degrees, the maximum principal strain increases again to approximately 0.27%.

Figure 11:
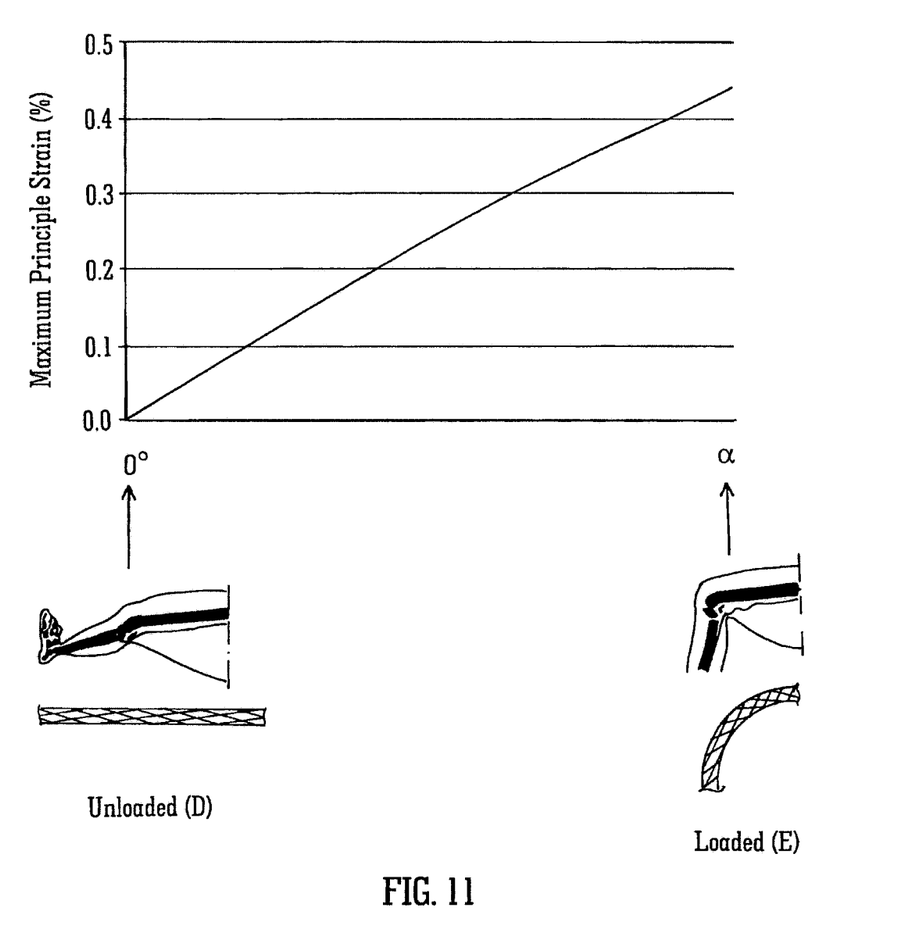
FIG. 11 shows a comparative example of a conventional stent at two configurations and a graph showing the maximum principal strains in the stent at different angles of deformation.

By way of comparison, FIG. 11 shows the case of an initially straight stent subject to the same loading. The strains are zero when the leg is not bent, but the maximum principal strain increases to 0.46% when the leg is bent to an angle of α degrees. Thus for the same loading, the straight stent will exhibit higher strains than the stent with geometry which is intermediate loaded and unloaded configurations.

During bending of the leg, the popliteal artery, which is the artery behind the knee, exhibits large degrees of bending, as seen in FIGS. 10 and 11. The lower superficial femoral artery, which is above the popliteal artery, exhibits bending and also experiences shortening. Conversely, when the leg moves from a sitting condition to a straight condition the arteries must extend over an increased distance. This can be seen in FIGS. 10 and 11.

The strains calculated and shown in FIGS. 10 and 11 relate to examples of stents. It will be appreciated that with different stent patterns (i.e. the pattern of struts or wires forming the stent) the equivalent calculations can be made and will show the same trends in strains when the stents are loaded in a similar manner.

Figures 4, 5:
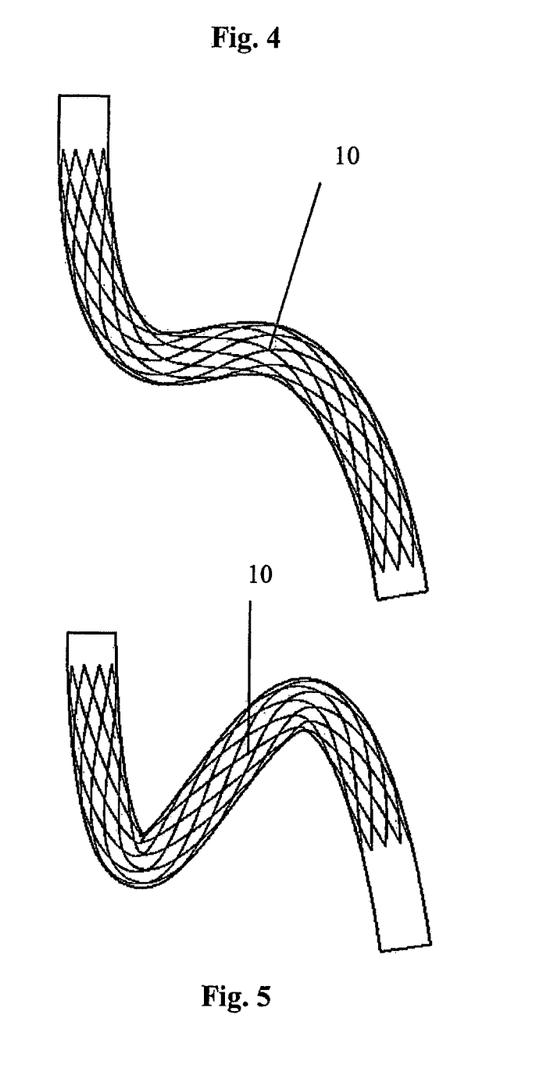
FIG. 4 is a side view of another medical device according to the invention in a first loaded configuration located in a body lumen.
FIG. 5 is a side view of the device of FIG. 4 in a second loaded configuration located in the body lumen.
Figure 6:
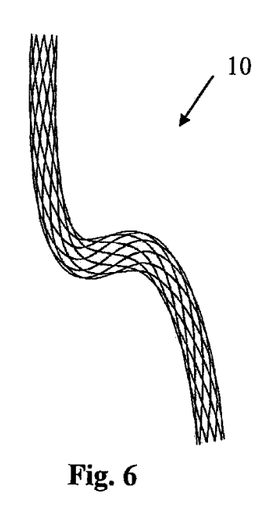
FIG. 6 is a side view of the device of FIG. 4 in an unloaded configuration.

In FIGS. 4 to 6 there is illustrated another medical device 10 according to the invention, which is similar to the medical device 1 of FIGS. 1 to 3. In this case the stent 10 is bendable through two bends between the first loaded configuration (FIG. 4) and the second loaded configuration (FIG. 5).

In the unloaded configuration the longitudinal axis of the stent 10 is curved through two bends in a two-dimensional plane (FIG. 6).

FIGS. 4 to 6 illustrate multiple bends in one plane. FIG. 4 illustrates the stent 10 deployed in the unloaded vessel, FIG. 5 illustrates the stent 10 deployed in the loaded vessel, and FIG. 6 illustrates the stent 10 in the unloaded configuration.

The curve embodied represents a configuration between the two opposing extremes of deformation of the blood vessel, such as those shown in FIGS. 4 and 5. In this case, the stent geometry, as shown in FIG. 6, represents a deformed state in between the straight unloaded state (FIG. 4) and the loaded state (FIG. 5).

Figure 7:
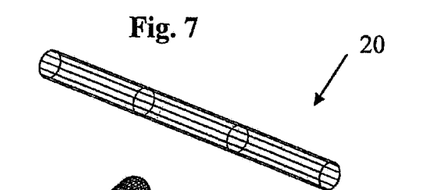
FIG. 7 is an isometric view of another medical device according to the invention in a first loaded configuration.
Figure 8:
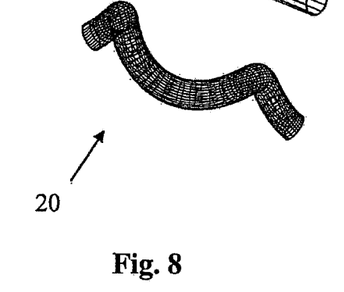
FIG. 8 is an isometric view of the device of FIG. 7 in a second loaded configuration.
Figure 9:
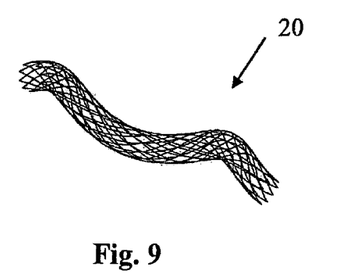
FIG. 9 is an isometric view of the device of FIG. 7 in an unloaded configuration.

FIGS. 7 to 9 illustrate a further medical device 20 according to the invention, which is similar to the medical device 1 of FIGS. 1 to 3.

In this case the stent 20 is bendable and twistable through multiple bends between the first loaded configuration (FIG. 7) and the second loaded configuration (FIG. 8).

In the unloaded configuration the longitudinal axis of the stent 20 is curved through multiple bends in three-dimensional space (FIG. 9). In this case in the unloaded configuration the stent 20 is helically shaped.

When the stent 20 is deployed in the blood vessel, the stent 20 exerts force on the blood vessel causing the blood vessel to adopt a helical configuration. In this manner the stent 20 acts to support at least part of the internal wall of the blood vessel in the helical configuration. Blood flowing through the helically shaped blood vessel then undergoes a swirling action. The swirling flow of blood has been found to minimise thrombosis and platelet adhesion, and to minimise or prevent coverage of the stent 20 by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

FIGS. 7 to 9 illustrate multiple bends of the blood vessel in two planes allowing the stent 20 to shorten in a controlled fashion and under lower strains. FIG. 7 illustrates the unloaded vessel, FIG. 8 illustrates the loaded vessel, and FIG. 9 illustrates the stent 20 in the unloaded configuration.

Figure 12:
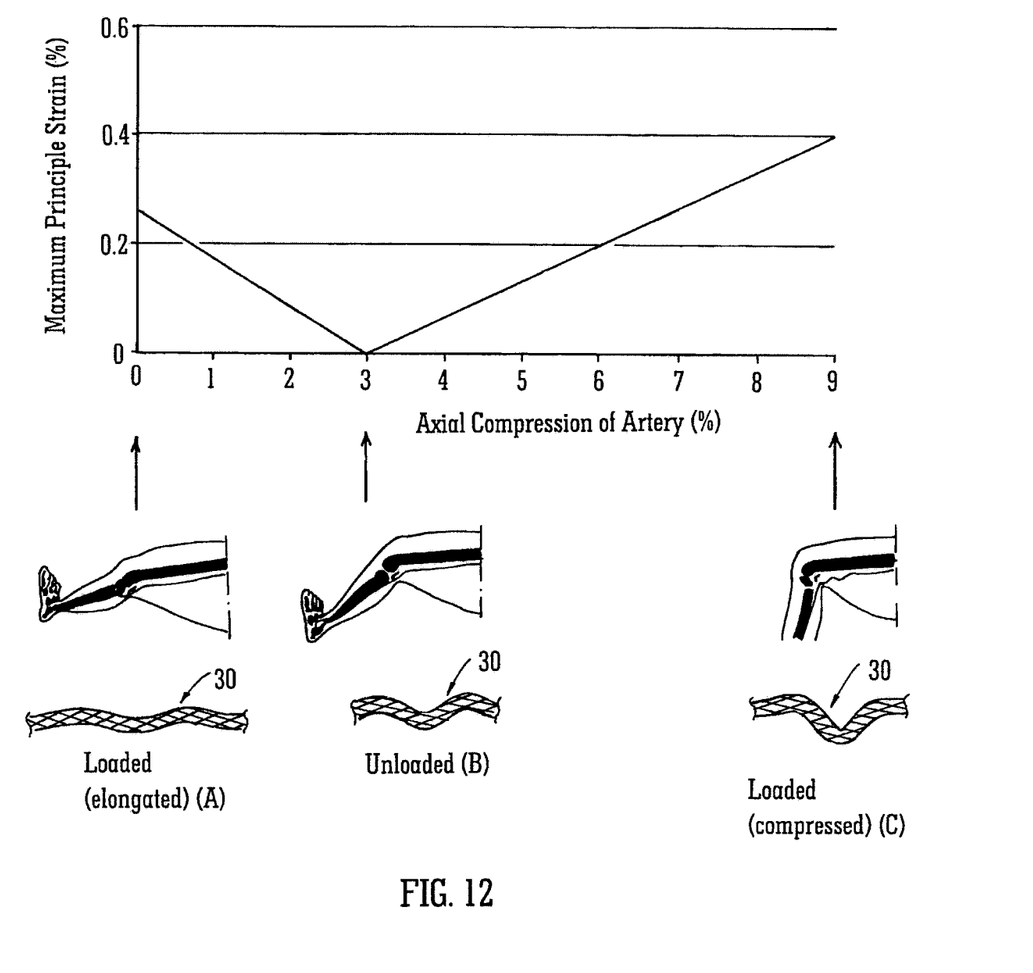
FIG. 12 shows three configurations of a stent with a helical longitudinal axis and a graph showing the maximum principal strains in the stent at different axial compressions.

FIG. 12 shows an example of a stent 30 having a helical longitudinal axis. In position A shown in FIG. 12, the helical stent is in a first loaded configuration, when the leg is straight. When the leg is partially bent, the stent is in an unloaded configuration shown at position B. When the leg is more bent, to a sitting position, the stent 30 is in a second loaded configuration. In position C the stent is axially compressed.

When the stent is in position B, in its unloaded configuration, it has a certain relative amplitude and helical pitch. In position A when the stent is in its elongated first loaded configuration, the relative amplitude is decreased and the pitch is increased. In position C, when the stent is axially compressed, the relative amplitude is increased and the pitch is decreased.

The strains which are induced in stent 30 were investigated using finite element analysis and the results are shown in the graph of FIG. 12. When the stent is first deployed in the straight leg, the stent is elongated due to the radial constraint of the artery. This induces a maximum principal strain of approximately 0.26%. Upon bending of the leg, the stented artery shortens into the helical geometry shown at position B. The stented artery has an axial compression of zero when the leg is straight and at position B it has approximately 3% compression. At that stage, the stent is in its unloaded configuration and strains in the stent are zero. Upon further bending of the leg, more axial compression of the stented artery is induced causing the stent to become more helical (increased relative amplitude and decreased pitch) and the maximum principal strain in the stent to increase to approximately 0.4% at 9% stented artery axial compression. This is shown at position C.

Figure 13:
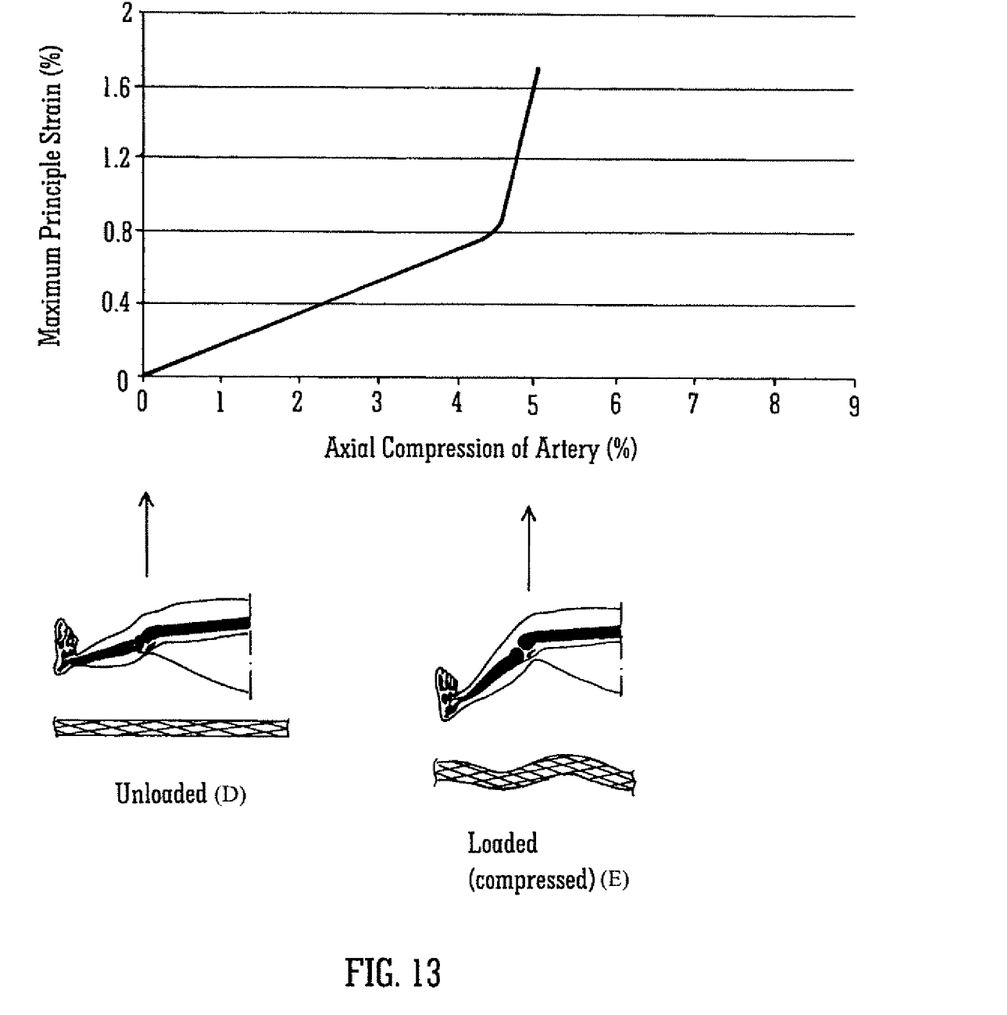
FIG. 13 shows a comparative example of a conventional stent at two configurations and a graph showing the maximum principal strains in the stent at different axial compressions.

FIG. 13 shows an example of a straight stent for comparison purposes. Such known stents are not designed to take up a helical geometry naturally. Position D shows the straight stent when the leg is straight. As the leg bends, finite element analysis predicts that the stent will buckle and kink causing strains in excess of 1.6%, as shown at position E in FIG. 13. This level of strain may cause a fracture of the stent.

Thus for the same loading, the straight stent will exhibit higher strains than the stent with geometry which is intermediate the loaded and unloaded configurations.

The strains calculated and shown in FIGS. 12 and 13 relate to examples of stents. It will be appreciated that with different stent patterns (i.e. the pattern of struts or wires forming the stent) the equivalent calculations can be made and will show the same trends in strains when the stents are loaded in a similar manner.

The helical longitudinal axis of a helical stent may follow a circular path when viewed from an end of the stent. The longitudinal axis may rotate around a central axis which is at the geometrical centre of an envelope in which the helical stent is contained. The central axis may be straight or may itself be curved, for example curved in a two-dimensional plane. The helical longitudinal axis of the stent may not necessarily be circular when viewed along the central axis, i.e. from an end of the stent. For example, the longitudinal axis could be elliptical to form an elliptical helix, or other curve in three-dimensional space. If the longitudinal axis is elliptical, then preferably the major axis of the ellipse is aligned with the plane in which the body part, such as a knee or elbow, bends.

FIGS. 10 and 11 show how an improved result can be obtained with a stent having a bend in one plane, whilst FIGS. 12 and 13 show how an improved result can be obtained with a stent having a longitudinal axis curved in three-dimensional space, e.g. helical. An improved result can similarly be obtained during compressive loading by a stent with multiple bends in one plane, for example having a sinusoidal or serpentine longitudinal axis. Such a stent is shown for example in FIGS. 4-6.

The geometries described, which are intermediate to the loaded and unloaded configurations, could also be manifested in a piecewise fashion, i.e. a series of straight sections along the stent, whose orientation varies with respect to one another, to achieve an overall curvature or series of bends along the stent. Thus the longitudinal axis of the stent overall could have a zig-zag shape or a saw tooth shape.

Figure 14:
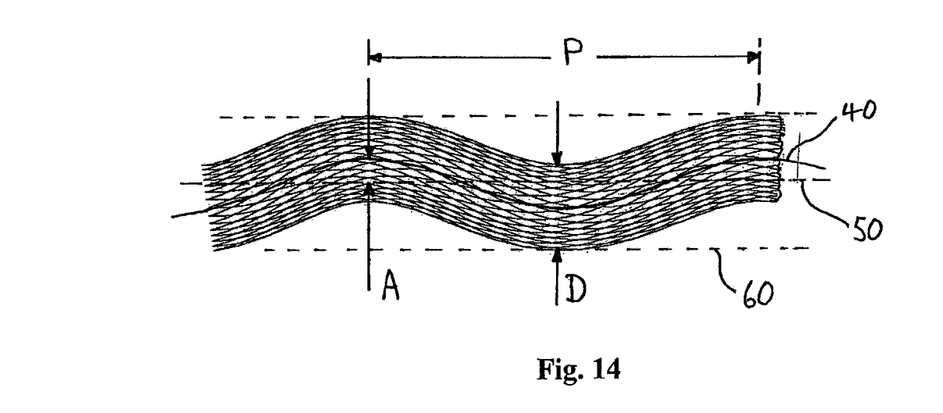
FIG. 14 shows part of a helical stent.

FIG. 14 shows part of a helical stent and explains some of the parameters used in this specification.

The stent shown in FIG. 14 has a circular cross-section, an internal diameter D and a wall thickness (not shown). The stent is shaped in a helix and has a longitudinal helical axis 40 which follows a helical path about a central longitudinal axis 50. The longitudinal helical axis 40 has an amplitude A (as measured from mean to extreme) and a pitch P. The stent is contained in an imaginary envelope 60 which extends longitudinally and has a width equal to the swept width of the stent. The central longitudinal axis 50 is at the centre of the envelope 60 and may also be referred to as an axis of helical rotation.

It will be appreciated that the stent may be moved between the first loaded configuration and the second loaded configuration under the action of any loading mode. For example the device may be deformed between the first loaded configuration and the second loaded configuration, and/or the device may be compressed between the first loaded configuration and the second loaded configuration.

The invention is not limited to the embodiments hereinbefore described, with reference to the accompanying drawings, which may be varied in construction and detail.

The invention claimed is:

1. A method of employing a medical device in a body lumen, wherein the medical device is a stent, comprising:
   deploying and expanding the stent in a body lumen, the stent having a diameter, the body lumen being deformable between an unloaded state and a loaded state wherein in the loaded state, the body lumen is more curved than in the unloaded state;
   wherein the stent is one which, after deployment and expansion, is deformable between a first loaded configuration and a second loaded configuration and has an unloaded configuration intermediate the first loaded configuration and the second loaded configuration;
   wherein in said unloaded and second loaded configurations at least part of the longitudinal axis of the stent is helically shaped and has an amplitude and wherein in the second loaded configuration the amplitude of the helical longitudinal axis divided by the diameter of the stent is greater than in the unloaded configuration;
   wherein the deploying comprises deploying the stent in the body lumen so that after deployment and expansion when the body lumen is in the unloaded state the stent is in the first loaded configuration, and when the body lumen is in the loaded state the stent is in the second loaded configuration;
   wherein in the unloaded configuration the amplitude of the helical longitudinal axis divided by the diameter of the stent is in the range of 0.3 to 0.9;
   wherein in the first loaded configuration at least part of the longitudinal axis of the stent is one of straight and helical and the amplitude of said part of the longitudinal axis divided by the diameter of the stent is in the range of 0 to 0.5; and
   wherein in the second loaded configuration the amplitude of the helical longitudinal axis divided by the diameter of the stent is in the range of 0.5 to 2.

2. A method as claimed in claim 1, wherein the pitch of the helical longitudinal axis is less in the second loaded configuration than in the unloaded configuration.

3. A method as claimed in claim 1, wherein in the first loaded configuration at least part of the longitudinal axis of the stent is helically shaped and the amplitude of the helical longitudinal axis divided by the diameter of the stent is less than in the unloaded configuration.

4. A method as claimed in claim 3, wherein the pitch of the helical longitudinal axis is greater in the first loaded configuration than in the unloaded configuration.

5. A method as claimed in claim 1, wherein the stent is bendable between the first loaded configuration and the second loaded configuration.

6. A method as claimed in claim 1, wherein the stent is twistable between the first loaded configuration and the second loaded configuration.

7. A method as claimed in claim 1, wherein the stent is compressible between the first loaded configuration and the second loaded configuration.

8. A method as claimed in claim 1, wherein the unloaded configuration is midway between the first loaded configuration and the second loaded configuration.

9. A method as claimed in claim 1, further comprising aligning the stent relative to the body lumen in which the stent is deployed.

10. A method as claimed in claim 9, wherein aligning the stent comprises aligning a marker or the stent with the body lumen.

11. A method as claimed in claim 1, wherein the body lumen is a blood vessel.

12. A method as claimed in claim 1, wherein the stent has a longitudinal axis with a length of at least 50 mm.

13. A method as claimed in claim 1, wherein the stent is made of Nitinol.

14. A method of employing a medical device in a body lumen, wherein the medical device is a stent, comprising:
  deploying and expanding the stent in a body lumen such that it is in a deployed, expanded configuration; and
  when the stent is in the deployed, expanded configuration:
  deforming the stent to a first loaded configuration, wherein when the stent is in the first loaded configuration, the body lumen is in an unloaded state;
  deforming the stent to a second loaded configuration, wherein when the stent is in the second loaded configuration, the body lumen is in a loaded state, which is more curved than the unloaded state of the body lumen;
  wherein the stent has an unloaded configuration intermediate the first and second loaded configurations and wherein in the unloaded and second loaded configurations at least part of the longitudinal axis of the stent is helically shaped, wherein the amplitude of the helical longitudinal axis divided by the diameter of the stent is greater in the second loaded configuration than in the unloaded configuration; and
  wherein when the stent is axially compressed by 6% from the first loaded configuration to the second loaded configuration, the maximum strain in the stent, at any stage at or between the first and second loaded configurations, is less than or equal to 0.7%.

15. A method as claimed in claim 14, wherein the maximum strain is less than or equal to 0.5%.

* * * * *